(12) United States Patent
Eramo, Jr. et al.

(10) Patent No.: US 8,378,011 B2
(45) Date of Patent: Feb. 19, 2013

(54) ENHANCED DURABILITY OF HYDROPHILIC COATINGS

(75) Inventors: Lincoln Eramo, Jr., Winchester, CA (US); James Campbell, Salt Lake City, UT (US); Paul Matlin, Salt Lake City, UT (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1147 days.

(21) Appl. No.: 11/964,908

(22) Filed: Dec. 27, 2007
(Under 37 CFR 1.47)

(65) Prior Publication Data
US 2009/0171302 A1 Jul. 2, 2009

(51) Int. Cl.
*C08G 18/80* (2006.01)
*C08G 18/83* (2006.01)
*C03C 25/10* (2006.01)
*B05D 5/10* (2006.01)
*B05D 1/40* (2006.01)

(52) U.S. Cl. ......... 524/86; 427/207.1; 427/331; 522/50; 522/102

(58) Field of Classification Search .................... 524/86; 522/50, 111, 162, 102; 427/207.1, 331
See application file for complete search history.

(56) References Cited

U.S. PATENT DOCUMENTS

| | | | |
|---|---|---|---|
| 4,439,583 A | 3/1984 | Gould et al. | |
| 5,077,372 A | 12/1991 | Hu et al. | |
| 5,091,205 A | 2/1992 | Fan | |
| 5,441,488 A | 8/1995 | Shimura et al. | |
| 5,503,631 A | 4/1996 | Onishi et al. | |
| 5,509,899 A | 4/1996 | Fan et al. | |
| 5,558,900 A | 9/1996 | Fan et al. | |
| 5,576,072 A | 11/1996 | Hostettler et al. | |
| 5,620,738 A | 4/1997 | Fan et al. | |
| 5,645,931 A | 7/1997 | Fan et al. | |
| 5,662,960 A | 9/1997 | Hostettler et al. | |
| 5,667,735 A | 9/1997 | Bae et al. | |
| 5,670,558 A | 9/1997 | Onishi et al. | |
| 5,693,034 A | 12/1997 | Buscemi et al. | |
| 5,731,087 A | 3/1998 | Fan et al. | |
| 5,756,144 A | 5/1998 | Wolff et al. | |
| 5,849,368 A | 12/1998 | Hostettler et al. | |
| 5,902,631 A | 5/1999 | Wang et al. | |
| 5,919,570 A | 7/1999 | Hostettler et al. | |
| 5,936,005 A | 8/1999 | Askienazy et al. | |
| 6,001,165 A * | 12/1999 | Shibuya et al. | 106/287.17 |
| 6,017,577 A | 1/2000 | Hostettler et al. | |
| 6,030,656 A | 2/2000 | Hostettler et al. | |
| 6,040,058 A | 3/2000 | Hostettler et al. | |
| 6,048,620 A | 4/2000 | Zhong | |
| 6,080,488 A | 6/2000 | Hostettler et al. | |
| 6,114,406 A | 9/2000 | Caiger et al. | |
| 6,120,904 A | 9/2000 | Hostettler et al. | |
| 6,139,510 A | 10/2000 | Palermo | |
| 6,161,630 A | 12/2000 | Stump et al. | |
| 6,176,849 B1 | 1/2001 | Yang et al. | |
| 6,218,016 B1 | 4/2001 | Tedeschi et al. | |
| 6,221,425 B1 | 4/2001 | Michal et al. | |
| 6,221,467 B1 | 4/2001 | Nazarova et al. | |
| 6,262,115 B1 | 7/2001 | Guittard et al. | |
| 6,265,016 B1 | 7/2001 | Hostettler et al. | |
| 6,299,980 B1 | 10/2001 | Shah et al. | |
| 6,436,540 B1 | 8/2002 | Garcia et al. | |
| 6,458,867 B1 | 10/2002 | Wang et al. | |
| 6,503,958 B2 | 1/2003 | Hughes et al. | |
| 6,506,823 B2 | 1/2003 | Burns et al. | |
| 6,528,150 B2 | 3/2003 | Nazarova et al. | |
| 6,540,698 B1 | 4/2003 | Ishii | |
| 6,589,215 B2 | 7/2003 | Yang et al. | |
| 6,610,035 B2 | 8/2003 | Yang et al. | |
| 6,648,874 B2 | 11/2003 | Parisi et al. | |
| 6,656,517 B2 | 12/2003 | Michal et al. | |
| 6,673,053 B2 | 1/2004 | Wang et al. | |
| 6,673,453 B2 | 1/2004 | Beavers et al. | |
| 7,008,979 B2 | 3/2006 | Schottman et al. | |
| 7,012,057 B2 | 3/2006 | Kapoor et al. | |
| 7,063,884 B2 | 6/2006 | Hossainy et al. | |
| 7,264,859 B2 | 9/2007 | Rouns et al. | |
| 7,534,495 B2 * | 5/2009 | Eramo | 428/424.2 |
| 2005/0054774 A1 | 3/2005 | Kangas | |
| 2005/0055044 A1 | 3/2005 | Kangas | |
| 2005/0170071 A1 | 8/2005 | Eramo | |
| 2007/0014945 A1 | 1/2007 | Lin et al. | |

FOREIGN PATENT DOCUMENTS

| | | |
|---|---|---|
| EP | 0591091 | 4/1994 |
| WO | 9529722 | 11/1995 |
| WO | 03046119 | 6/2003 |

OTHER PUBLICATIONS

Lubrizol Technical Data Sheet, Sancure 1073C Aliphatic Waterborne Urethane Polymer, 1 page, Jun. 4, 2007.
Lubrizol Product Bulletin, Tecogel TPU, 1 page, Jun. 2007.

* cited by examiner

Primary Examiner — Harold Pyon
Assistant Examiner — Atnaf Admasu
(74) Attorney, Agent, or Firm — Seager, Tufte & Wickhem, LLC

(57) ABSTRACT

Lubricous coatings, methods for making and using lubricous coatings, and medical device that include lubricious coatings. An example lubricous coating may include a hydrophilic polymer, a flow modifier, an acrylic monomer, a photoinitiator, and a solvent. The coating can be used to coat a medical device along an inner surface, an outer surface, or an intermediate surface.

24 Claims, 3 Drawing Sheets

ENHANCED DURABILITY OF HYDROPHILIC COATINGS

FIELD OF THE INVENTION

The invention relates to lubricious coatings. More particularly, the invention relates to lubricous coatings for use with medical devices.

BACKGROUND

A wide variety of lubricous coatings have been developed, for example, for use with medical devices. Of the known lubricous coatings, each has certain advantages and disadvantages. There is an ongoing need to provide alternative lubricous coatings, methods for making and using lubricous coatings, and medical devices with lubricious coatings.

BRIEF SUMMARY

The invention provides design, material, and manufacturing method alternatives for lubricious coatings and medical devices with lubricious coatings. The coatings can be used to coat a medical device along an inner surface, an outer surface, or an intermediate surface.

An example lubricous coating may include a hydrophilic polymer, a flow modifier, an acrylic monomer, a photoinitiator, a solvent, and a binder.

Another example lubricous coating material may include polyethylene oxide, a flow modifier, an acrylic monomer, a photoinitiator, and isopropyl alcohol.

An example medical device may include an elongate shaft and a lubricious coating disposed on the shaft. The lubricious coating may include a hydrophilic polymer, a silane, a flow modifier, a photoinitiator, and an acrylic monomer. The acrylic monomer may be cross-linked to form an interpenetrating network.

Another example lubricious coating material may include a hydrophilic polymer, a silane, a flow modifier, a photoinitiator, aziridine, and an acrylic monomer that is cross-linked to form an interpenetrating network.

An example method for forming a lubricious coating material may include mixing together a hydrophilic polymer, a silane, a flow modifier, a photoinitiator, aziridine, and an acrylic monomer and cross-linking the acrylic monomer to form an interpenetrating network.

Some additional details regarding these and other embodiments are described in more detail below.

The above summary of some embodiments is not intended to describe each disclosed embodiment or every implementation of the present invention. The Figures and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

DETAILED DESCRIPTION

Figure 1:
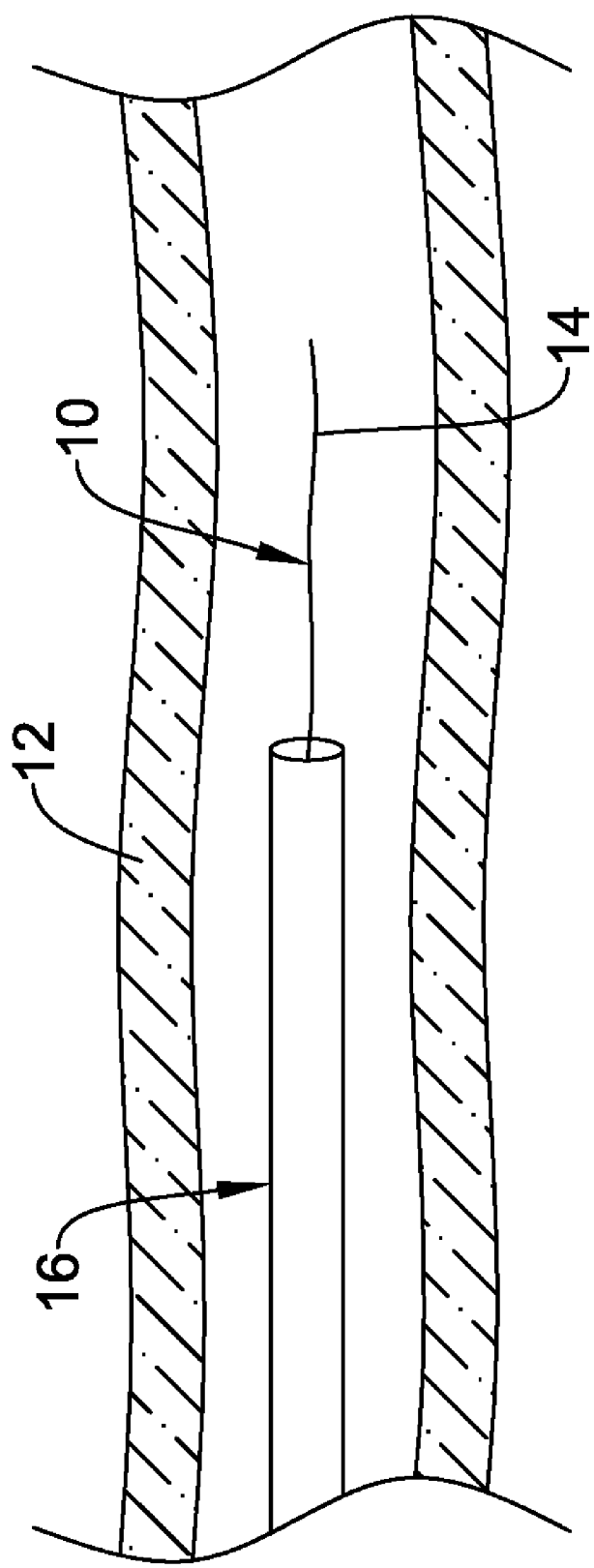
FIG. 1 is side view of an example catheter and guidewire disposed within a blood vessel.

The following description should be read with reference to the drawings wherein like reference numerals indicate like elements throughout the several views. The detailed description and drawings illustrate example embodiments of the claimed invention.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Weight percent, percent by weight, wt %, wt-%, % by weight, and the like are synonyms that refer to the concentration of a substance as the weight of that substance divided by the weight of the composition and multiplied by 100.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

FIG. 1 is a plan view of an example guidewire 10 disposed in a blood vessel 12. Guidewire 10 may include a distal section 14 that may be, as is well known in the art, generally configured for probing deep within the anatomy of a patient. Guidewire 10 may be used for intravascular procedures according to common practice and procedure. For example, guidewire 10 may be used in conjunction with another medical device such as a catheter 16. Of course, numerous other uses are known amongst clinicians for guidewires and other similarly configured medical devices.

Because many medical devices are designed to function within the vasculature, it is often desirable to coat the medical devices with a coating, for example, that is lubricious, hydrophilic, protective, and/or the like. Lubricious coatings have a lower coefficient of friction than other non-lubricious or less lubricous materials. This gives lubricious materials or coatings a smooth, slippery feel that is desirable for some applications. Accordingly, a lubricious coating can improve device handling, exchanges and steerability, and improve lesion crossing capability. Although coatings are typically associated with intravascular guidewires and catheters, such as the ones schematically represented in FIGS. 1-3, essentially any medical device may benefit from a coating. It can be appreciated that the coated medical device could be any intravascular device or be any device designed to pass through or be disposed in an opening or body lumen. For example, the device may comprise any type of guidewire, catheter (e.g., therapeutic, diagnostic, or guide catheter), endoscopic device, laproscopic device, stent or stent-associated device, embolic protection device, or any other suitable device.

Lubricious polymers typically utilized for medical devices include silicone, high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like. Hydrophilic polymers may be blended among themselves or with formulated amounts of water insoluble compounds (including some polymers) to yield coatings with suitable lubricity, bonding, and solubility.

Because metals (e.g., stainless steel and nickel-titanium alloy, and the like) are commonly used in the manufacturing of medical devices, the lubricous coating is often applied to a metal. One of the manufacturing challenges in making these medical devices is related to the durability of the lubricious coating. For example, the lubricious coating may not bond well with the particular metal chosen. Manufactures address this concern, for example, by scoring the surface of the metal so that lubricious coating may more durably bond to the medical device. The present invention relates to alternative lubricious coatings, methods for making and using lubricious coatings, and medical devices that utilize these coatings. In at least some embodiments, the inventive lubricious coatings have enhanced durability as well as add a number of other desirable features as explained in more detail below.

In at least some embodiments, an example lubricious coating may include a hydrophilic polymer, a flow modifier, an acrylic monomer, a photoinitiator, a solvent, and a binder. Another example lubricious coating material may include polyethylene oxide, a flow modifier, an acrylic monomer, a photoinitiator, and isopropyl alcohol. Another example lubricious coating material may include a hydrophilic polymer, a silane, a flow modifier, a photoinitiator, aziridine, and an acrylic monomer that is cross-linked to form an interpenetrating network. Examples of each of the components of the various coating materials are described below. The coating may be applied to and/or disposed on a suitable substrate such as, for example, a surface on a medical device to provide the substrate with the desired characteristics.

Some of the materials that make up the lubricious coating may form a "semi-interpenetrating network" (SIPN) or an "interpenetrating network" (IPN). This may help to overcome or otherwise reduce some the manufacturing challenges that can be associated with coating, for example, medical devices. Therefore, utilizing a lubricious coating that forms a SIPN and/or an IPN may enhance the durability of the coating. The SIPN or IPN may take the form of a web of material that may function by holding the lubricious coating and/or components thereof onto the substrate (e.g., a medical device surface). In some embodiments the SIPN/IPN may be formed by cross-linking and/or polymerizing the acrylic monomer. By doing so, the cross-linked/polymerized acrylic monomer may form a web that can hold the lubricous coating or the remaining components thereof on a medical device surface. In at least some embodiments, the SIPN/IPN may be thought of as forming a physical or mechanical "bond" or structure that may hold the remaining components of the lubricious coating on the appropriate substrate.

Hydrophilic Polymers

The lubricious coating may include a hydrophilic polymer that may add the desired lubricous characteristics to the coating. The hydrophilic polymer may be present in a suitable quantity such as about 1-15 wt-%. Some examples of hydrophilic polymers, include, but are not limited to, polyalkylene glycols and alkoxy polyalkylene glycols; copolymers of methylvinyl ether and maleic acid; maleic anhydride polymers; polylkylene oxides, such as the polyethylene oxides; poly((meth)acrylic acids); polymers of hydroxyl-substituted lower alkyl(meth)acrylates, such 2-hydroxyalkyl(meth)acrylate; polyvinylalcohols, hydrophilic polyamides; poly(meth) acrylamides; poly(N-isopoly(meth)acrylamides); poly(sodium-4-styrenesulfonates) and poly(sodium vinylsulfonates); poly(3-hydroxybutyric acids); poly(N-vinyl lactams) such as the polyvinylpyrrolidones; hydrophilic polyurethanes; polyethyleneimines; poly(sodium(meth) acrylates); methyl cellulose, hydroxylmethyl cellulose, hydroxyethyl cellulose; polyvinylsulfonic acid; heparin; dextran and dextan sulfate and other modified dextrans; poly (saccharides); chondroitin sulphate; lecithin; and the like, as well as copolymers thereof, and mixtures thereof. Some additional hydrophilic polymers are described in U.S. Pat. Nos. 6,458,867 and 6,503,958, the entire disclosures of which is herein incorporated by reference.

Hydrophilic polyurethanes, for example aliphatic polyether polyurethanes, which have high water absorbency being capable of absorbing anywhere from about 500% to about 2000% water by weight, may also be used for the lubricious coating either alone or in combination with hydrophilic polymers. These types of polyurethanes are described in U.S. patent application Ser. No. 10/658,718, the entire disclosure of which is herein incorporated by reference. These polymers may be advantageously blended with polyurethanes having lesser water absorbency.

Hydrogel polymers may also be used either alone or in combination with any of the other materials listed above. The above list of hydrophilic lubricants include some of those materials that may be classified as "hydrogels". Hydrogels are known to absorb water and become slippery upon exposure to an aqueous environment. Examples of the hydrogels include, but are not limited to, polyethylene oxide, polyacrylic acid, polyacrylamides, poly(sodium-4-styrenesulfonates), poly(3-hydroxybutyric acids), polyvinylpyrrolidones, 2-hydroxyethyl methacrylates, and the like. Hydrogels are discussed in U.S. Pat. No. 5,693,034, the entire disclosure of which is herein incorporated by reference.

The molecular weights of the hydrophilic polymers described above may range anywhere from about 1,000 g/mole to 1,500,000 g/mole or more. The weight average molecular weight of such polymers may be from about 75,000 g/mole to about 1,000,000 g/mole or about 100,000 g/mole to about 750,000 g/mole. See for example, U.S. Pat. No. 6,262,115, which discusses molecular weights of some hydrogels, the entire disclosure of which is herein incorporated by reference.

Hydrophobic materials may also be employed instead of or in addition to hydrophilic polymers. Some examples of hydrophobic polymers include silicones (i.e. organosiloxane polymers), functionalized silicones, hydrolyzable silanes which form silicones, fluorosilanes and other fluoropolymers, cellulose esters and ethers, ethyl cellulose, cellulose nitrate, cellulose acetate, cellulose acetate butyrate, cellulose acetate propionate, hydrophobic polyurethanes, polyacrylates, natural and synthetic elastomers, polyacetals, hydrophobic polyamides, polyvinylidene chloride, polycarbonate, homopolymers and copolymers of vinyl compounds, polyvinylchloride, glycerin, olive, vegetable, and other natural oils, and so forth. Some of these materials also form a gel-like substance, such as some silicones.

Flow Modifiers

Examples of suitable flow modifiers, but are not limited to, acrylic flow modifiers, fine silica powders, fine barium sulfate powders, fine particulate organic resins, clay-containing flow modifiers, polyamide-containing flow modifiers, urea-containing flow modifiers, urethane-containing flow modifiers, polycarboxylic acid salt-containing flow modifiers, cellulose-containing flow modifiers and so forth. In at least some embodiments, the flow modifier may be MODAFLOW® AQ3025, available from Solutia, St. Louis, Mo. Flow modifiers may be used in amounts of about 0.01 wt-% to about 5 wt-%, or about 0.05 wt-% to about 1 wt-%, or about 0.05 wt-% to about 0.2 wt-%.

Acrylic Monomers

The lubricious composition may include an acrylic monomer. The acrylic monomers may form the SIPN/IPN when cross-linked and/or polymerized, which may enhance the durability of the coating. An example acrylic monomers is an alkoxylated (meth)acrylate having at least two acrylate or methacrylate groups, and suitably three or more (meth)acrylate groups. The amount of alkoxylation is suitably from about 1 to about 20 moles, about 2 to about 20 moles, about 3 to about 20, about 2 to about 18 moles, or about 3 to about 15 moles of alkoxylation. Examples of suitable alkoxylate groups include both propoxylates and ethoxylates as well as mixtures thereof.

Examples of suitable bi-, tri-, tetra-, etc. polyfunctional alkoxylated or polyalkoxylated acrylates include alkoxylated, for example ethoxylated or propoxylated, neopentyl glycol diacrylates, butanediol diacrylates, trimethylolpropane tri-acrylates glyceryl triacrylates, and the like.

In at least some embodiments, an alkoxylated trimethylol propane triacrylate monomer is employed, suitably an ethoxylated trimethylol propane triacrylate. Such compounds are available from Sartomer Company, Inc. in Exton, Pa. Examples include SR454 having 3 moles of ethoxylation, a molecular weight of 454 g/mole and a water solubility of 15 wt-% in water; SR499 having 6 moles of ethoxylation and a molecular weight of 560 g/mole; SR502 having 9 moles of ethoxylation and a molecular weight of 693 g/mole and SR9035 having 15 moles of ethoxylation and a molecular weight of 956 g/mole. Such compounds may also be found from Aldrich Chemical Co., Inc. in Milwaukee, Wis. having from 1 mole of alkoxylate and greater.

Other examples of suitable alkoxylated (meth)acrylate compounds include, but are not limited to, propoxylated trimethylol propane tri(meth)acrylate, ethoxylated pentaerythritol tetra(meth)acrylate, propoxylated neopentyl glycol diacrylate, propoxylated gylceryl tri(meth)acrylate, trimethylolpropane ethoxylate (1 EO/OH) methyl ether diacrylate, and the like.

The alkoxylated (meth)acrylate compounds may have a water solubility of about 15 wt-% or more, or about 50 wt-% or more. The aromatic alkoxylated (meth)acrylates tend to have little or no water solubility. For example, ethoxylated bisphenol A di(meth)acrylate, is classified as alkali soluble. However, this is not to say that some of the aromatic acrylates do not have water solubility and thus, if so, they may also be employed herein.

The acrylic monomers may be employed in amounts of about 0.01 wt-% to about 5 wt-%, or about 0.05 wt-% to about 1 wt-%, or about 0.05 wt-% to about 0.2 wt-%.

These polymerizable materials (i.e., the acrylic monomers) are typically cured through the addition of actinic radiation such as ultraviolet (UV) radiation, e-beam radiation, or laser beam radiation may also be employed. The ethoxylated (meth)acrylate compounds, for the most part, cure via a free radical mechanism. They also may be sensitive to oxygen and can form stable radicals in its presence. Thus, it may be advantageous to employ an inert gas purge.

Photoinitiators

Crosslinking and/or polymerizing may be facilitated by the addition of a photoinitiator. Any photoinitiator which is suitable for use in free radical curing mechanisms may be employed herein. Examples of suitable photoinitiators include, but are not limited to, benzophenones, acrylated amine synergists, ketone type, i.e. aromatic-aliphatic ketone derivatives, including benzoin and its derivatives, benzil ketals, .alpha.-amino ketones, and so forth. Additional examples of photoinitiators suitable for use herein include, but are not limited to, 2-phenyl-1-indanone; IRGACURE® 184 from Ciba Specialty Chemicals, BENACURE® 184 from Mayzo and SARCURE® SR1122 from Sartomer, all of which are 1-hydroxylcyclohexylphenyl ketone (HCPK); BENACURE® BP benzophenone; BENACURE® 651 and IRGACURE® 651, both of which are benzil dimethyl ketal or 2,2' dimethoxy-2-phenylacetophenone; BENACURE® 1173 2-hydroxy-2-methyl-1-phenyl-1-propanone; IRGACURE® 907 2-methyl 1-[4-methylthio)phenyl]2-morpholinopropan-1-one; IRGACURE® 369 morpholinoketone; and so forth and blends thereof.

Photoinitiators are also available commercially in a variety of blends. Examples of commercially available blends include, but are not limited to, SARCURE® SR1136 is a blend of 4-methylbenzophenone and benzophenone; SARCURE® SR1137 is a blend of trimethylbenzophenone and methylbenzophenone; BENACURE® 500, a blend of 1-hydroxylcyclohexylphenyl ketone and benzophenone;

In some embodiments, a ketone or α-amino ketone type of photoinitiator may be utilized when the acrylic crosslinker is a (meth)acrylate type compounds. Examples of suitable α-amino ketone photoinitiators include, but are not limited to, 2-methyl 1-[4-methylthio) phenyl]2-morpholinopropan-1-one, 2-benzyl-2-(dimethylamine)-1-[4-morpholi-nyl)phenyl]-1-butanone or a mixture thereof.

It has been found that the α-amino ketone photoinitiators may be employed advantageously with any ethylenically unsaturated monomer and second lubricity providing component to arrive at an improved photocurable interpenetrating network. See for example, commonly assigned copending U.S. patent application Ser. No. 10/658,729, the entire content of which is incorporated by reference herein in its entirety. In some other embodiments, α-amino ketone photoinitiators can be used in combination with a polymerizable ethylenically unsaturated resin and at least one second component which provides lubricity.

Mixtures of any of the above photoinitiators may also be employed. Photoinitiators or blends thereof are typically used in amounts of about 0.001 wt-% to about 5 wt-%, or about 0.002 wt-% to about 0.1 wt-%, or about 0.002 wt % to about 0.005 wt-%.

Solvents

In preparing the solution mixture of the present invention, the hydrophilic polymer and the acrylic monomer are mixed in a solvent or cosolvent mixture. Examples of suitable organic solvents include, but are not limited to, the lower alcohols such as isopropyl alcohol, methanol, and ethanol. Other suitable solvents or cosolvents include water; linear or cyclic carboxamides such as N,N-dimethylacetamide (DMAC), N,N-diethylacetamide dimethylformamide (DMF), ethyl formamide, diethylformamide; N-methyl-2-pyrrolidone (NMP); dimethylsulphoxide (DMSO); acetonitrile; acetone and acetyl acetone; acrylonitrile; benzonitriledimethyl acetamide; 1,4-dioxane; dipropyl sulfone; aromatic solvents such as toluene and xylene; nitrobenzene; phenylacetate; propionitrile; combinations thereof, and the like. The solvents or cosolvent mixtures may be employed in amounts of about 50 wt-% to about 99.9 wt-%, or about 75 wt-% to about 99.9 wt-%, or about 85 wt-% to about 99.9 wt-%.

Other suitable organic solvents include, but are not limited to, aliphatic, cycloaliphatic or aromatic ether-oxides, more particularly dipropyl oxide, diisopropyl oxide, dibutyl oxide, methyltertiobutylether, ethylene glycol dimethylether (glyme), diethylene glycol dimethylether (diglyme); phenyl oxide; dioxane, tetrahydrofuran (THF). Of course, any mixtures of the above-described solvents, i.e. cosolvent blends, may also be employed.

Surfactants may be employed to obtain a satisfactory mixture in the solvent or cosolvent blend. Any soluble surfactant or a mixture of surfactants in the above-mentioned solvents may be useful. Surfactants may be advantageous where hydrophobic and hydrophilic materials, or otherwise incompatible materials, are being mixed with one another.

Binders

As indicated above, the crosslinked and/or polymerized materials (e.g., the cross-linked/polymerized acrylic monomer) may form a SIPN and/or an IPN. The SIPN/IPN may help to hold the cross-linked acrylic monomer onto, for example, a portion of the medical device to which the coating is applied. In addition, a binder may also be added that may increase the overall durability and lubricity of the lubricious coating. In at least some embodiments, the binder material is soluble in isopropyl alcohol but insoluble in water. Accordingly, when one adds the binder to the lubricious coating, the binder helps to press the lubricious coating onto the substrate by swelling in the presence of water, but not dissolving. In addition, the binder bonds with the hydrophilic polymer. This helps to keep or hold the hydrophilic polymer within a matrix and also improves the overall durability of the lubricious coating.

An example binder is acrylic acid-styrene copolymer with a molecular weight of about 3000 to about 15,000 and an acid number of about 50-200. Some examples of acrylic acid-styrene copolymers that may be utilized as binders include JONCRYL® polymers, commercial available from Johnson Polymer, Sturtevant, Wis., such as JONCRYL ECO® 675, JONCRYL ECO® 684, JONCRYL ECO® 694, JONCRYL ECO® 2117, JONCRYL ECO® 2124, JONCRYL ECO® 2177, JONCRYL ECO® 2189, JONCRYL DFC® 3015, JONCRYL DFC® 3025, JONCRYL DFC® 3030, JONCRYL DFC® 3040E, JONCRYL DFC® 3050E, and JONCRYL DFC® 3060.

In at least some embodiments, about 0.01 wt-% to about 25 wt-% of the binder may be utilized, or about 5 wt-% to about 15 wt-%, or about 8 wt-% to about 12 wt-%.

Other Components

Other optional additives may be employed in combination with the present invention including, but not limited to, viscosity modifiers, antioxidants, coupling agents, and so forth.

Examples of suitable coupling agents include, but are not limited to, silanes (e.g., Dow Z-6020), titanates, zirconates, and so forth. At least some of these materials, for example silane, may bind well to metal. Coupling agents may be employed in amounts of about 0.01 wt-% to about 5 wt-%, more suitably about 0.01 wt-% to about 1 wt-%, and most suitably about 0.01 wt-% to about 0.1 wt-% based on a solvent or cosolvent blend of the composition.

In some embodiments, an additional crosslinker may be utilized to form a second interwoven crosslinked species. The additional crosslinker may be a thermal crosslinker such as aziridine (propyleneimine), commercially available as CX-100 Aziridine from NeoResins. This material may be desirable because it crosslinks with polyethylene oxide. Accordingly, the two interwoven crosslinked species may include crosslinked polyethylene oxide (or another hydrophilic polymer) as well as crosslinked acrylic copolymer.

Methods for Applying the Lubricous Coating and Addition Example Uses for the Lubricious Coating The lubricious coating may be applied to the medical device by any method known in the art including, but not limited to, spraying, dipping, painting, rolling, sponge painting, and so forth. This may include coating an interior surface (i.e., along lumen), an exterior surface, or any intermediate surface. Once applied, the "wet" coating may be cured by exposing it to UV light (e.g., using a Xenon Bulb Curing System "B" bulb) for about 4-60 seconds, for example. This may cause and/or initiate the cross-linking, for example by means of free-radical and other polymerization reactions, of the acrylic monomer into, in theory, one large web. The coating may also be allowed to dry and for the solvent to be removed, for example, by evaporation leaving only the solids of the coating behind. The solvent may be more readily evaporated at an elevated temperature, although room temperature drying is acceptable. However, in at least some embodiments, improved durability may be achieved by drying the coating at elevated temperatures of, for example, 50-90° C. (e.g., 70° C.). Drying at an elevated temperature over several hours may also improve the durability of the coating. Crosslinkers which have a high enough molecular weight and which are not highly volatile, can be compounded directly with lubricant, allowing the use of extrusion or coextrusion techniques for applying the coating. Such techniques may not require the use of solvents.

Additional Schematic Representations of Further Uses for Lubricious Coatings

Figure 2:
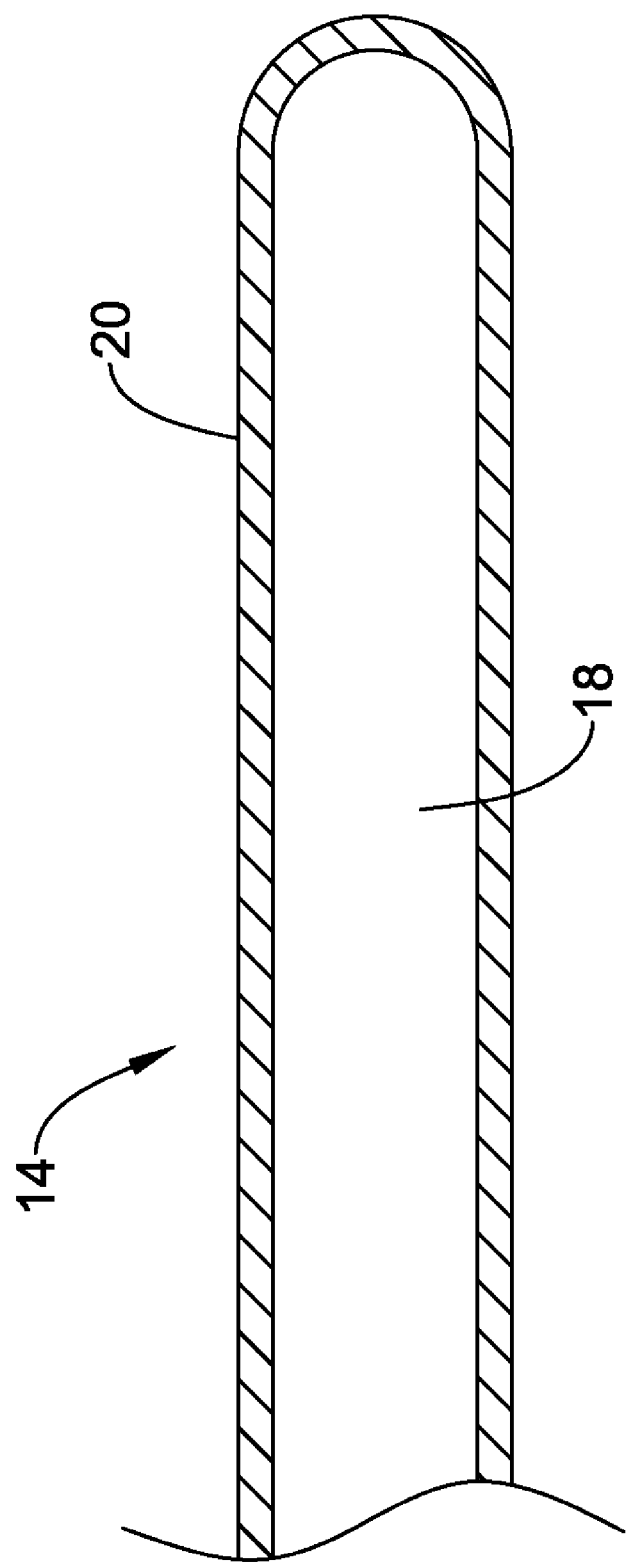
FIG. 2 is a side view of an example guidewire including a lubricious coating.
Figure 3:
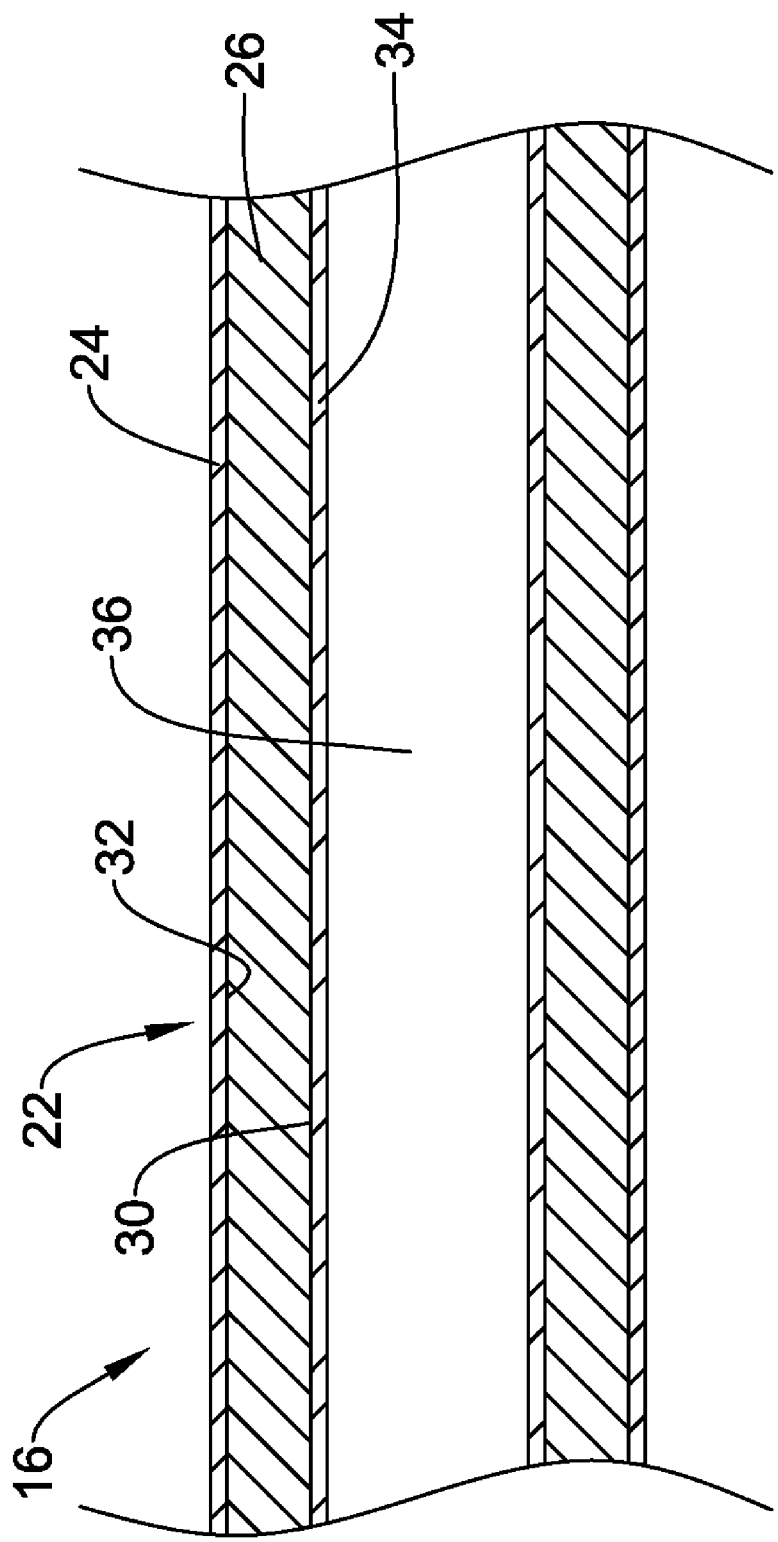
FIG. 3 is a side view of an example catheter including a lubricious coating.

FIGS. 2 and 3 depict examples of some other medical devices that include the lubricious coating as described herein. For example, FIG. 2 is a partial cross-sectional side view of guidewire 14 having a core or body portion 18 and a lubricious coating 20 disposed thereon. Lubricious coating 20 is similar in form and function to the lubricious coating described above. Core or body portion 18 may be a core wire or any other configuration suitable for a guidewire as this figure is merely meant to demonstrate that lubricious coating 20 may be used with guidewires.

FIG. 3, similarly, depicts catheter 16 having a catheter shaft body 22. Here, catheter shaft 22 may include a lubricious coating 24 similar to coating 20 disposed on an exterior surface 32 of a core region 26. Alternatively, or in conjunction with this, another lubricious coating 34 may be disposed along an interior surface 30 of core region 26 so that coating 34 is disposed along a lumen 36 defined by core region 26. Core region 26 may be a tubular member or other catheter component that defines a portion of the catheter. This figure demonstrates that a number of different surfaces (e.g., interior, exterior, or intermediate) of a number of medical devices may be coated with any of the lubricious coatings disclosed herein.

As described above, the disclosed lubricious coating may be utilized with a number of different medical devices and is not intended to be limited to only catheters and guidewires. Moreover, the schematic representations of guidewire 14 and catheter 16 are not intended to limit the application of the inventive lubricious coating to any particular style of guidewire or catheter as the lubricious coating may be utilized in a wide variety of catheters and guidewires.

EXAMPLES

The invention may be further clarified by reference to the following Examples, which serve to exemplify some of the preferred embodiments, and not to limit the invention in any way.

Example 1

An example lubricious coating was formed by combining the following:
  78.2 g isopropyl alcohol
  2.4 g polyethylene oxide (900,000 g/mol)
  20 g reverse osmosis H₂O
  0.1 g Flow Modifier, Modaflow® AQ3025, acrylic copolymer
  0.025 g Silane, Dow Z-6020
  0.8 g acrylic monomer, Sartomer SR9035
  0.03 g photoinitiatior, Irgacure 907
  0.1 g aziridine, Neoresins, CX-100

The polyethylene oxide was mixed with isopropyl alcohol and H₂O, and it was dissolved. The flow modifier was then added to increase the flow characteristics of the viscous polyethylene oxide solution. Silane was added to the mixture, which is known to bind well to metal. Next, the acrylic monomer was added. Then, the photoinitiator was added as to serve as the catalyst for the reaction—it was dispersed throughout the mixture. This "wet" lubricious coating was then applied to a substrate. Then the coating was cured by exposing it to UV light (e.g., using a Xenon Bulb Curing System "B" bulb) for about 15-45 seconds. This caused the cross-linking, for example by means of free-radical and other polymerization reactions, of the acrylic monomer into, in theory, one large web. The isopropyl alcohol evaporated as did the H₂O, leaving behind only solids. This formed the lubricious coating on the substrate.

Example 2

Another example lubricious coating was formed by combining the following:
  78.2 g isopropyl alcohol
  1.8 g polyethylene oxide (900,000 g/mol)
  20 g reverse osmosis H₂O
  0.1 g Flow Modifier, Modaflow® AQ3025, acrylic copolymer
  0.025 g Silane, Dow Z-6020
  0.4 g acrylic monomer, Sartomer SR9035
  0.015 g photoinitiatior, Irgacure 907
  0.6 g styrene/carboxilic acid copolymer binder material, JONCRYL 67

The polyethylene oxide was mixed with isopropyl alcohol and H₂O, and it was dissolved. The flow modifier was then added to increase the flow characteristics of the viscous polyethylene oxide solution. Silane was added to the mixture, which is known to bind well to metal. Next, the acrylic monomer was added. Then, the photoinitiator was added as to serve as the catalyst for the reaction—it was dispersed throughout the mixture. The binder material was also added. This "wet" lubricious coating was then applied to various substrates including guidewires and/or guidewire components as well as catheters and/or catheter components. Then the coating was cured by exposing it to UV light (e.g., using a Xenon Bulb Curing System "B" bulb) of UV light for about 15-45 seconds. This caused the cross-linking, for example by means of free-radical and other polymerization reactions, of the acrylic monomer into, in theory, one large web. The isopropyl alcohol evaporated out of the coating once it was applied to the substrate, and the H₂O did as well, leaving behind only solids. This formed the lubricious coating on the substrate.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A lubricious coating material, comprising:
   a hydrophilic polymer;
   a binder substantially insoluble in water, wherein the binder swells in the presence of water;
   a flow modifier;
   an acrylic monomer, wherein upon polymerization the acrylic monomer forms an interpenetrating network;
   a photoinitiator; and
   a solvent.

2. The coating material of claim 1, wherein the hydrophilic polymer includes polyethylene oxide.

3. The coating material of claim 1, wherein the binder includes acrylic acid-styrene copolymer.

4. The coating material of claim 1, where the binder is soluble in isopropyl alcohol.

5. The coating material of claim 1, wherein the acrylic monomer includes ethoxylated trimethylol propane triacrylate esters.

6. The coating material of claim 1, wherein the photoinitiator includes 2-methyl-1-[4-(methylthio)phenyl]-2-(4-morpholinyl)-1-propanone.

7. The coating material of claim 1, wherein the solvent includes water.

8. The coating material of claim 1, wherein the solvent includes an organic solvent.

9. The coating material of claim 8, wherein the solvent includes isopropyl alcohol.

10. The coating material of claim 9, wherein the solvent further includes water.

11. The coating material of claim 1, further comprising silane.

12. The coating material of claim 1, further comprising aziridine.

13. A lubricious coating material, comprising:
    polyethylene oxide;
    a flow modifier;
    a binder substantially insoluble in water, wherein the binder swells in the presence of water;
    an acrylic monomer, wherein upon polymerization the acrylic monomer forms an interpenetrating network;
    a photoinitiator; and
    isopropyl alcohol;
    wherein the interpenetrating network forms a web that holds the lubricious coating material on a substrate.

14. The coating material of claim 13, wherein the coating material includes about 1-15 wt-% polyethylene oxide.

15. The coating material of claim 13, wherein the coating material includes about 50-99.9 wt-% isopropyl alcohol.

16. The coating material of claim 13, further comprising aziridine.

17. The coating material of claim 13, further comprising a silane.

18. A medical device, comprising:
    an elongate shaft;
    a lubricious coating disposed on the shaft; and
    wherein the lubricious coating includes a hydrophilic polymer, a silane, a flow modifier, a photoinitiator, and an acrylic monomer, and wherein the acrylic monomer is cross-linked to form an interpenetrating network.

19. The medical device of claim 18, wherein the lubricious coating is disposed along an outer surface of the shaft.

20. The medical device of claim 18, wherein the shaft defines a lumen and an inner surface along the lumen, and wherein the lubricous coating is disposed along the inner surface.

21. The medical device of claim 18, wherein the lubricious coating is disposed along an intermediate surface of the shaft.

22. A lubricious coating material, comprising:
   a hydrophilic polymer;
   a silane;
   a flow modifier;
   a photoinitiator;
   aziridine; and
   an acrylic monomer that is cross-linked to form an interpenetrating network.

23. A method for forming a lubricious coating material, the method comprising:
   mixing together a hydrophilic polymer, a silane, a flow modifier, a photoinitiator, aziridine, and an acrylic monomer; and
   cross-linking the acrylic monomer to form an interpenetrating network.

24. The method of claim 23, wherein cross-linking the acrylic monomer to form an interpenetrating network includes exposing the acrylic monomer to UV light.

* * * * *